United States Patent
Vicario et al.

(10) Patent No.: US 11,247,009 B2
(45) Date of Patent: Feb. 15, 2022

(54) ANOMALY DETECTION DEVICE AND METHOD FOR RESPIRATORY MECHANICS PARAMETER ESTIMATION

(71) Applicant: KONINKLIJKE PHILIPS N.V., Eindhoven (NL)

(72) Inventors: Francesco Vicario, Boston, MA (US); Antonio Albanese, New York, NY (US); Dong Wang, Scarsdale, NY (US); Nicolas Wadih Chbat, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 912 days.

(21) Appl. No.: 15/769,364

(22) PCT Filed: Oct. 13, 2016

(86) PCT No.: PCT/IB2016/056115
§ 371 (c)(1),
(2) Date: Apr. 19, 2018

(87) PCT Pub. No.: WO2017/068464
PCT Pub. Date: Apr. 27, 2017

(65) Prior Publication Data
US 2018/0304034 A1      Oct. 25, 2018

Related U.S. Application Data

(60) Provisional application No. 62/243,174, filed on Oct. 19, 2015.

(51) Int. Cl.
*A61M 16/00*     (2006.01)
*A61B 5/00*      (2006.01)
*A61B 5/087*     (2006.01)

(52) U.S. Cl.
CPC .......... *A61M 16/024* (2017.08); *A61B 5/087* (2013.01); *A61B 5/4836* (2013.01);
(Continued)

(58) Field of Classification Search
CPC ..... A61B 5/087; A61B 5/4836; A61B 5/7239; A61B 5/7264; A61B 5/7282;
(Continued)

(56) References Cited

U.S. PATENT DOCUMENTS

| 2009/0221926 A1* | 9/2009 | Younes | A61M 16/026 |
| | | | 600/529 |
| 2011/0297155 A1* | 12/2011 | Shelly | A61M 16/024 |
| | | | 128/204.23 |

(Continued)

FOREIGN PATENT DOCUMENTS

| EP | 1515767 B1 | 8/2009 |
| WO | 2007131314 A1 | 11/2007 |

(Continued)

OTHER PUBLICATIONS

Vicario et al: "Noninvasive Estimation of Respiratory Mechanics in Spontaneously Breathing Ventilated Patients: A Constrained Optimization Approach"; IEEE Transactions On Biomedical Engineering, vol. 63, No. 4, Apr. 2016, pp. 775-787.

(Continued)

*Primary Examiner* — Valerie L Woodward
(74) *Attorney, Agent, or Firm* — Daniel H. Brean (57) ABSTRACT

A mechanical ventilation device (10) includes a mechanical ventilator. At least one airway sensor (24, 26) is configured to measure at least one of airway pressure and airway air flow as a function of time for a patient on the mechanical ventilator. At least one microprocessor (28, 30) is programmed to analyze at least one of airway pressure and airway air flow measured by the airway sensor to detect a (Continued)

spontaneous respiration anomaly in respiratory muscle pressure as a function of time generated by a patient on the mechanical ventilator. A display component (22) is configured to display an indication of a spontaneous respiration anomaly detected by the anomaly detection component.

19 Claims, 4 Drawing Sheets (52) U.S. Cl.
CPC .......... *A61B 5/7239* (2013.01); *A61B 5/7264* (2013.01); *A61B 5/7282* (2013.01); *A61M 16/0051* (2013.01); *A61M 16/026* (2017.08); *A61M 2016/0027* (2013.01); *A61M 2016/0036* (2013.01); *A61M 2205/18* (2013.01); *A61M 2205/502* (2013.01); *A61M 2205/581* (2013.01); *A61M 2205/583* (2013.01); *A61M 2230/06* (2013.01); *A61M 2230/30* (2013.01); *A61M 2230/42* (2013.01); *A61M 2230/46* (2013.01)

(58) Field of Classification Search
CPC .............. A61M 16/024; A61M 16/026; A61M 16/0051; A61M 2016/0027; A61M 2016/0036

See application file for complete search history.

(56) References Cited

U.S. PATENT DOCUMENTS

| 2012/0037159 A1* | 2/2012 | Mulqueeny ........... A61M 16/06 128/204.23 |
| 2014/0034054 A1* | 2/2014 | Angelico .......... A61M 16/0003 128/204.23 |
| 2014/0296728 A1* | 10/2014 | Sinderby ................. A61B 5/24 600/529 |
| 2015/0059754 A1 | 3/2015 | Chbat et al. |

FOREIGN PATENT DOCUMENTS

| WO | 2016128846 A1 | 8/2016 |
| WO | 2016166709 A1 | 10/2016 |

OTHER PUBLICATIONS

Younes et al: "A Method for Monitoring and Improving Patient: Ventilator Interaction"; Intensive Care Med (2007) 33:1337-1346.

\* cited by examiner

ANOMALY DETECTION DEVICE AND METHOD FOR RESPIRATORY MECHANICS PARAMETER ESTIMATION

CROSS-REFERENCE TO PRIOR APPLICATIONS

This application is the U.S. National Phase application under 35 U.S.C. § 371 of International Application No. PCT/IB2016/056115, filed on Oct. 13, 2016, which claims the benefit of U.S. Provisional Patent Application No. 62/243,174, filed on Oct. 19, 2015. These applications are hereby incorporated by reference herein.

FIELD

The following relates to the medical therapy arts, respiratory therapy arts, medical ventilation arts, and related arts.

BACKGROUND

In a spontaneously breathing patient receiving mechanical ventilation, the goal is to configure the mechanical ventilator to support the patient's spontaneous respiration. To this end, it is desirable to minimize patient-ventilator dyssynchrony. Some examples of potentially problematic patient-ventilator dyssynchrony include early cycling off and double effort. In early cycling off, the ventilator cycles off, so as to begin the expiration phase, before the patient completes his or her inspiration effort. In double effort, the patient makes two distinct inhalation efforts in a single inspiration period. Active exhalation is another condition that is useful to detect. During normal respiratory effort, the patient's diaphragm operates to expand the lungs to cause inhalation; the exhalation phase is normally passive and relies upon the elastance of the respiratory system to expel air from the lungs. In active exhalation, the patient's respiratory muscles actively operate to compress the lung volume during exhalation. These and other respiratory anomalies are difficult to assess for a patient on mechanical ventilation because the patient's respiratory effort is normally not measured.

The need for estimation of the respiratory system parameters (e.g., resistance R and elastance E) and patient inspiratory efforts (e.g., respiratory muscle pressure $P_{mus}$) is well-known in the medical community. Estimating $P_{mus}$ as a function of time ($P_{mus}(t)$) is especially important in patient-ventilator support modalities of mechanical ventilation, such as a Pressure Support Ventilation (PSV) mode, where a patient and a ventilator share the mechanical work performed on the respiratory system. A quantitative assessment of $P_{mus}(t)$ can be used to select the appropriate level of ventilation support delivered by the ventilator in order to prevent both atrophy and fatigue of patient respiratory muscles. The clinical parameter commonly used to assess the effort made by the patient per breath is known as Work of Breathing (WoB) and can be computed once the estimate of $P_{mus}(t)$ is available for the breath. WoB can be obtained from $P_{mus}(t)$ by integration of the latter over the inhaled volume. However, respiration anomalies can occur during mechanical ventilation, which can result in an inaccurate estimation of $P_{mus}(t)$ R, and/or E. Detecting such anomalies can improve the estimation of these parameters.

The following provides new and improved systems and methods which overcome the foregoing problems and others.

BRIEF SUMMARY

In accordance with one aspect, a mechanical ventilation device includes a mechanical ventilator. At least one airway sensor is configured to measure at least one of airway pressure and airway air flow as a function of time for a patient on the mechanical ventilator. At least one microprocessor is programmed to analyze at least one of airway pressure and airway air flow measured by the airway sensor to detect a spontaneous respiration anomaly in respiratory muscle pressure as a function of time generated by a patient on the mechanical ventilator. A display component is configured to display an indication of a spontaneous respiration anomaly detected by the anomaly detection component.

In accordance with another aspect, a non-transitory storage medium stores instructions readable and executable by one or more microprocessors to perform a method of detecting a spontaneous respiration anomaly. The method includes detecting peaks in an airway pressure versus time signal acquired for a patient on a mechanical ventilator; and detecting a patient-ventilator dyssynchrony indicated, for instance, by a double peak in the airway pressure versus time signal within a single breath.

In accordance with another aspect, a method of detecting a spontaneous respiration anomaly includes detecting peaks in an airway pressure versus time signal acquired for a patient on a mechanical ventilator; and detecting a patient-ventilator dyssynchrony indicated by a double peak in the airway pressure versus time signal within a single breath.

One advantage resides in improved monitoring for anomalies in patient respiratory effort during mechanical ventilation of a spontaneously respiring patient.

Another advantage resides in detecting such an anomaly in patient respiratory effort without determining the patient respiratory muscle pressure $P_{mus}(t)$.

Another advantage resides in automatically adjusting settings of a ventilator responsive to a detected anomaly.

Another advantage resides in classifying breaths into favorable and unfavorable breaths from the perspective of the estimation of respiratory mechanics.

Further advantages of the present invention will be appreciated to those of ordinary skill in the art upon reading and understand the following detailed description. It will be appreciated that any given embodiment may achieve none, one, more, or all of the foregoing advantages and/or may achieve other advantages.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Estimates of R (resistance) and E (elastance) of the respiratory system are important since they provide quantitative information to a physician about the mechanical properties of the patient's respiratory system. They can also be used to diagnose respiratory diseases and better select the appropriate ventilation modalities and therapeutic paths.

Moreover, R and E can also be used to non-invasively estimate $P_{mus}(t)$ (respiratory muscle pressure) as a non-invasive alternative to the use of an esophageal catheter. Assuming R and E are known, it is indeed possible to estimate $P_{mus}(t)$ via the following equation (known as the Equation of Motion of the Lungs):

$$P_{aw}(t)=R\dot{V}(t)+EV(t)+P_{mus}(t)+P_0 \quad (1)$$

where $P_{aw}$ is the pressure measured at a Y-piece of the ventilator (also known as pressure at the airway opening or mouth of the patient), $\dot{V}$ is the flow of air into and out of the patient respiratory system (measured again at the Y-piece), V is the net volume of air delivered by the ventilator to the patient (measured by integrating the flow signal over time), $P_0$ is a constant term to account for the pressure at the end of expiration/start of inhalation. In addition, 1/E is often indicated as C (respiratory system compliance). In some embodiments, $P_{mus}(t)$ is estimated simultaneously with R and E, relying on equation (1).

The inventors have found, however, that typical respiratory system parameters estimation algorithms can produce inferior results for mechanically ventilated patients under certain conditions, such as early ventilator cycling off, patient's double effort, and patient's active exhalation. Such respiratory effort anomalies are also often clinically problematic or call for corrective adjustment of the mechanical ventilator settings, e.g. adjusting the ventilator cycling to improve alignment with respiratory effort. Accordingly, detecting such anomalies has substantial benefits apart from improving respiratory system parameter estimation.

One or more algorithms in accordance with one aspect of the present disclosure can show occurrences of inferior estimation results for mechanically ventilated patients under certain conditions indicative of a spontaneous respiration anomaly in respiratory muscle pressure ($P_{mus}(t)$). The respiration anomalies can be detected by analyzing the airway pressure. The air flow may also be impacted by these anomalies and thus may also be analyzed, but since air flow responds to these anomalies more slowly than airway pressure, stronger signatures are expected to be observed in the airway pressure signal. Such anomalies can include early cycling off, double effort, and active exhalation. These anomalies can also be referred to as a patient ventilator dyssynchrony.

As used herein, the term "early cycling off" refers to a spontaneous respiration anomaly in which the ventilator cycles off before the patient's respiratory effort ceases.

As used herein, the term "double effort" refers to a spontaneous respiration anomaly in respiratory muscle pressure in which the patient makes two distinct breath efforts in a single (ventilator) breath cycle.

As used herein, the term "active exhalation" refers to a spontaneous respiration anomaly in respiratory muscle pressure when that patient actively assists exhalation rather than passively allowing the elasticity of the lungs to push air out.

The present disclosure provides an anomaly detection algorithm that detects, for each breath, if the ventilator cycles off before the patient effort is over. In embodiments that further include estimation of respiratory parameters using an Equation of Motion of the Lungs, a flag may be raised if such an anomaly is detected to indicate that the estimates of R, E and $P_{mus}(t)$ for that breath might be unreliable. The advantage of complementing respiratory mechanics estimation methods with anomaly detection algorithms is twofold. First, early cycling off of the ventilator is not a desirable clinical condition. Following detection of early cycling off, the clinician may choose to adjust the ventilator settings to align better with the patient's inspiration effort. The adjustment of settings can in some embodiments be automatically done by a closed-loop controller. Second, the anomaly potentially affecting the presented non-invasive respiratory system parameter estimation technique would be detected to the benefit of the overall estimation method performance. The concept can be extended to other ventilation anomalies that may adversely impact the respiratory mechanics estimation methods, such as active exhalation and double patient effort within the same breath.

Figure 1:
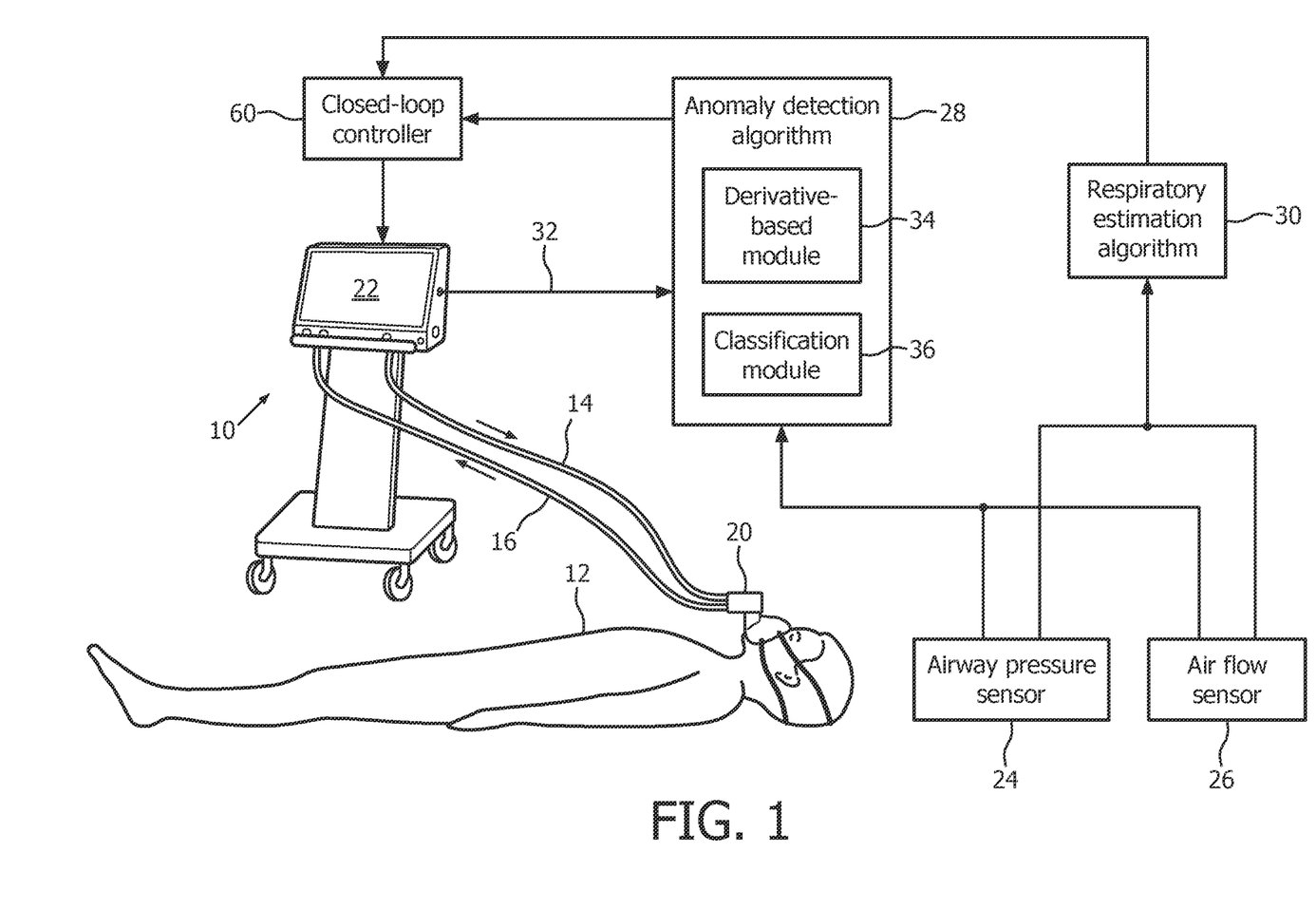
FIG. 1 diagrammatically shows a medical ventilation system including respiratory effort anomaly detection.

With reference to FIG. 1, an illustrative mechanical ventilation device is used to provide mechanical ventilation to a patient via a mechanical ventilator 10 that delivers air flow and/or pressure in accordance with ventilator settings to a ventilated patient 12 via an inlet air hose 14. Exhaled air returns to the ventilator 10 via an exhalation air hose 16. A Y-piece or T-piece 20 (or alternatively a tracheal tube) couples air from the discharge end of the inlet air hose 14 to the ventilated patient 12 during inhalation and couples exhaled air from the ventilated patient 12 into the exhalation air hose 16 during exhalation. Not shown in FIG. 1 are numerous other ancillary components that may be provided depending upon the ventilation mode and other therapy being received by the ventilated patient 12. Such ancillary components may include, by way of illustration: an oxygen bottle or other medical-grade oxygen source for delivering a controlled level of oxygen to the air flow, usually controlled by a Fraction of Inspired Oxygen ($FiO_2$) ventilator setting; a humidifier plumbed into the inlet line 14; a nasogastric tube to provide the patient 12 with nourishment; and so forth. The mechanical ventilator 10 has a user interface including, in the illustrative example, a touch-sensitive display component 22 via which the physician, respiratory specialist, or other medical personnel can visualize the ventilator settings and monitor measured physiological variables (e.g., airway pressure and air flow) and operating parameters of the mechanical ventilator 10. Additionally or alternatively, the user interface may include physical user input controls (buttons, dials, switches, et cetera), a keyboard, a mouse, audible alarm device(s), indicator light(s), or so forth.

Figure 2:
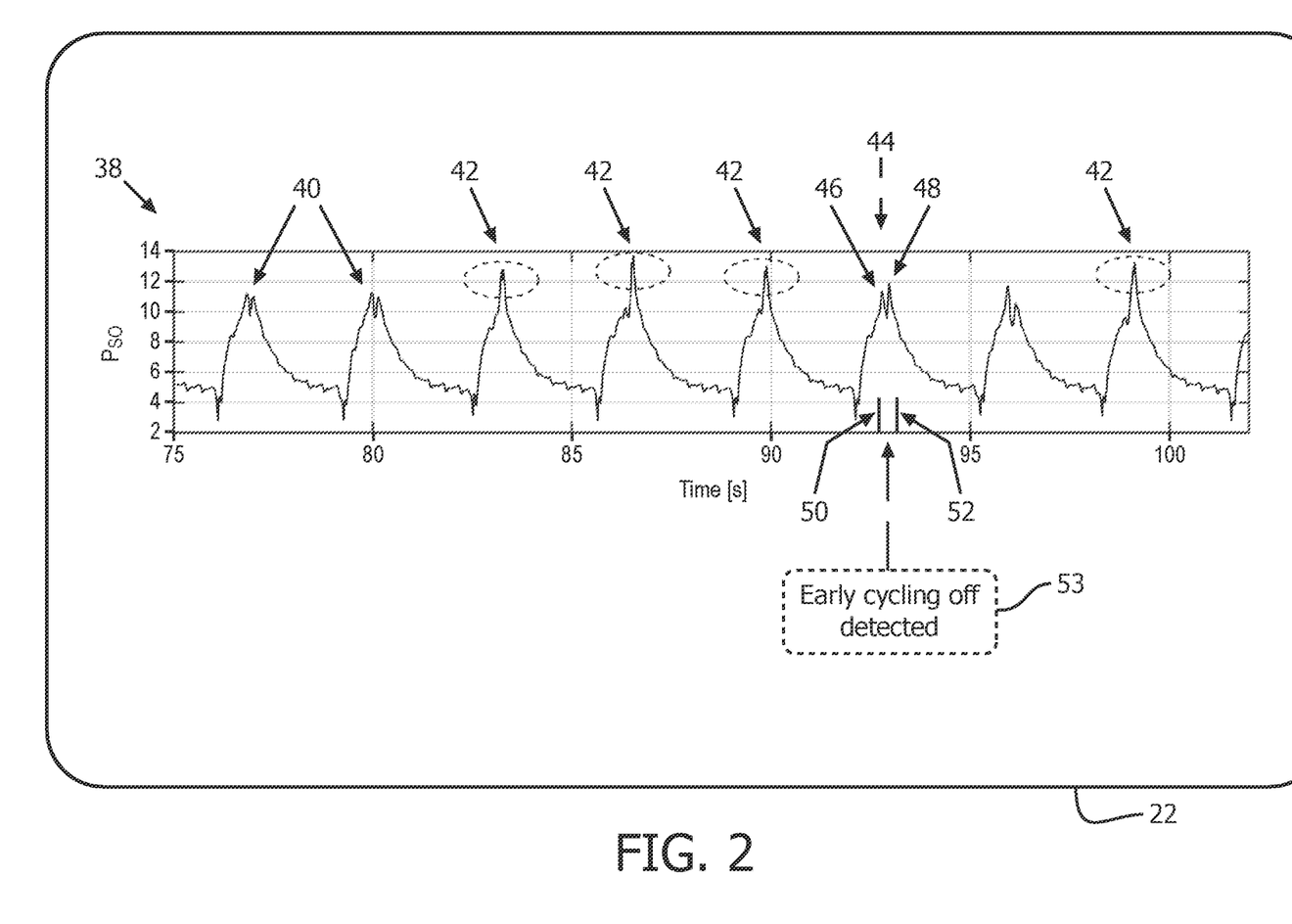
FIG. 2 shows a signal that is analyzed by one or more algorithms of the medical ventilation system of FIG. 1.

FIG. 1 diagrammatically illustrates a system for detecting a spontaneous respiration anomaly of the ventilated patient 12. For example, the mechanical ventilator 10 includes or is in communication with at least one air way sensor 24, 26. These sensors 24, 26 are shown diagrammatically in FIG. 1 and may, for example, be installed on the tubing 14, 16 or inside the ventilator unit 10. The at least one air way sensor 24, 26 is configured to measure at least one of airway pressure and airway air flow as a function of time for the patient 12 on the mechanical ventilator 10. For example, an airway pressure sensor 24 is configured to measure airway pressure as a function of time, and an airway air flow sensor 26 is configured to measure air flow as a function of time. The sensors 24, 26 are configured to measure airway pressure or air flow at the Y-piece 20 or at another appropriate point in the ventilator air flow circuit. It will be appreciated that only one of the sensors 24, 26 can be included, although usually both airway pressure and flow are monitored during mechanical ventilation. The data values of air pressure and/or air flow may be displayed on the display component 22 as an airway pressure (or air flow) versus time signal (e.g., a graphical signal), as numerical values updated in real time, or so forth. This data values of air pressure and/or air flow are also transferred to an anomaly detection algorithm 28 and, optionally, to a respiratory mechanics estimation algorithm 30 via a communication network (e.g., a wireless network, a local area network, a wide area network, a personal area network, BLUETOOTH®, and the like). Alternatively, the anomaly detection algorithm 28 and optional respiratory mechanics estimation algorithm 30 may be built into the mechanical ventilator 10 (e.g., executing on a microprocessor or microcontroller of the ventilator 10) in which case data from the sensors 24, 26 are collected by the ventilator 10 and hence available to the algorithms 28, 30. In another contemplated embodiment, the anomaly detection algorithm 28 and optional respiratory mechanics estimation algorithm 30 are implemented on the microprocessor of a patient monitor (not shown) that displays vital signs such as heart rate, respiration rate, blood pressure, or so forth, and the output of these algorithms 28, 30 are suitably displayed on the patient monitor display component.

The anomaly detection algorithm 28 is configured to receive as input the measured values of air pressure and/or air flow for the ventilated patient 12. The anomaly detection algorithm 28 receives a start-of-breath signal 32 from the ventilator 10 to enable delineation of breath intervals. Alternatively, the airway pressure or air flow signal can be segmented into breath intervals based on expected features (e.g., start of breath is indicated by a rapid increase in airway pressure and air flow). The anomaly detection algorithm 28 is programmed to analyze airway pressure and/or airway air flow measured by the airway sensor 24, 26 to detect a spontaneous respiration anomaly in respiratory muscle pressure as a function of time (i.e., $P_{mus}(t)$) generated by the patient 12 on the mechanical ventilator 10. The anomalies include at least an early cycling off anomaly, an active exhalation anomaly, and a double effort anomaly. To do so, the anomaly detection algorithm 28 is programmed to detect one or more peaks in an airway pressure (or air flow) versus time signal (see FIG. 2). For example, the anomaly detection algorithm 28 can include any suitable peak detection hardware (e.g., a peak detector circuit with a diode and a capacitor) or software (e.g., a Matched Filtration with Experimental Noise Determination algorithm, a vectorized peak detection algorithm, a least-squares curve-fitting algorithm, an optimization peak detection algorithm, a derivative-based algorithm, or the like). In illustrative embodiments described herein, the anomaly detection algorithm 28 uses a derivative-based module 34 to detect peaks of an airway pressure (or air flow) versus time signal (not shown in FIG. 1). It will be appreciated that the derivative-based module 34 also includes any suitable algorithms for signal processing processes (e.g., filtering, signal to noise ratio reduction, data smoothing, and the like). As described in more detail below, the derivative-based module 34 is configured to identify one or more anomalies based on abnormal peak detection readings, as described in more detail below. The derivative-based module 34 is configured to detect peak values (e.g., "y-axis" values of an airway pressure versus time signal, as described in more detail below) and the associated time values (e.g., "x-axis values") at which these peaks occur, as described in more detail below.

As shown in FIG. 1, the anomaly detection algorithm 28 also includes a classification module 36. The classification module 36 is configured to receive an indication of an abnormal peak detection reading from the derivative-based module 34. From the abnormal peak detection reading, the classification module 36 is configured to determine the type of spontaneous respiration anomaly (e.g., double effort, early cycling off, and active exhalation). The classification module 36 then "flags" the anomaly, and assigns a corresponding flag value to the type of anomaly, as described in more detail below. The flag value is an indication of a spontaneous respiration anomaly detected by the derivative-based module 34. The flag value is then transmitted to, and displayed on, the display component 22.

FIG. 2 shows one example display of an airway pressure versus time signal 38 shown on the display 22 of the mechanical ventilator 10. The airway pressure data 38 are taken from "Noninvasive Estimation of Respiratory Mechanics in Spontaneously Breathing Ventilated Patients: A Constrained Optimization Approach", *IEEE Trans Biomed Eng.,* 2015 (DOI 10.1109/TBME.2015.2470641). The signal 38 is based on experimental animal (i.e., pig) data. However, the signal 38 can instead be an air flow versus time signal. For illustrative and conciseness purposes only, the foregoing is described in regards to an airway pressure versus time signal. The anomaly detection algorithm 28 is programmed to detect at least one peak 40 of the signal 38. For example, the anomaly detection algorithm 28 is programmed to analyze airway pressure measured by the airway pressure sensor 24 to detect a spontaneous respiration anomaly as a double peak in the airway pressure as a function of time within a single breath cycle. A breath of the signal 38 with a double peak configuration is indicative of a spontaneous respiration anomaly, while a breath with a single peak configuration in the signal is considered "normal." The rationale underlying this approach is the expectation that, if the patient's inspiration effort is a normal single exertion and the positive pressure applied by the ventilator 10 is well-aligned with the patient's effort, then the airway pressure should exhibit a single peak corresponding to the nearly coincident termination of pressure applied by the ventilator and of the respiratory effort applied by the patient. On the other hand, if the ventilator cycles off early, then a double peak is expected the first peak being due to the ventilator cycling off and thereby removing its applied pressure, and a second anomalous peak due to the subsequent end of patient respiratory effort. Similarly, a double effort by the patient will be observed as two peaks attributable to the patient's two inspiration efforts.

As shown in FIG. 2, at least one single (i.e., normal) peak 42 is indicative that the respiratory muscles of the patient 12 were completely released before the ventilator 10 cycled off. In other words, when the muscles are released, $P_{mus}(t)$ rapidly returns back to 0. FIG. 2 shows an illustrative example. In this example, a normal breath has peaks with values ranging between approximately 13.0-14.0 cmH$_2$O. In this example, the mechanical ventilator is operating in Pressure Support Ventilation (PSV) mode with pressure set around 10 cmH$_2$O. When the patient releases the respiratory muscles, the corresponding change in effort $\Delta P_{mus}$ generates an increase in the airway pressure leading to peak airway pressures that are 3-4 cmH$_2$O higher than the 10 cmH$_2$O setpoint. By contrast, referring back to the Equation of the Lungs (Equation (1)), if the ventilator 10 cycles off before patient effort is over, $P_{aw}(t)$ first decreases immediately after the positive pressure applied by the ventilator is removed (i.e., from cycling off of the ventilator) and then increases due to quick release of patient effort $\Delta P_{mus}$ (i.e., from patient effort), giving rise to a second (and lower) peak in the measured signal 38 over a single breath, as indicated by 44.

The anomaly detection algorithm 28 is programmed to analyze airway pressure measured by the airway pressure sensor to detect a spontaneous respiration anomaly comprising an early cycling off event as a double peak in the airway pressure as a function of time coincident with the mechanical ventilator 10 cycling off. In particular, early cycling off is observed in the airway pressure waveform as a double peak in an airway pressure versus time signal acquired for the patient 12 on the mechanical ventilator 10 at about the time the ventilator cycles off. Normal breaths can be identified as the largest peak observed in the breath cycle (so that the double peak signifying early cycling off is a splitting of the largest peak of the breath cycle into two peaks), and/or the ventilator 10 can send a signal to the anomaly detection algorithm 28 when the ventilator 10 cycles off. The abnormal double peak 44 is due to an initial decline due to removal of the applied ventilator pressure followed by a second peak due to the release of patient respiratory effort after the ventilator has cycled off. The ventilator 10 only applies a positive pressure, so although pressure is controlled by the ventilator 10 in PSV mode, the ventilator cannot prevent (i.e. suppress) the second peak produced by the patient effort. To analyze the signal 38, the derivative-based module 34 is configured to find each of the peaks 40 (e.g., the normal peaks 42 and the abnormal peaks 44) of the signal 38. The abnormal peaks 44 include a first peak 46 and a second peak 48. The first peak 46 is indicative of cycling off of the ventilator (i.e., early cycling off), and the second peak 48 is indicative of continued effort by the patient 12. The derivative-based module 34 then sends this data (i.e., the data associated with each of the peaks 42 and 44) to the classification module 36.

The classification module 36 then analyzes the signal 38 to determine a type of anomaly. In the example shown in FIG. 2, the signal 38 includes multiple abnormal peaks 44, each of which includes the first and second peaks 46 and 48. Due to the positioning of the first and second peaks 46 and 48 (described above), the classification module 36 determines that the abnormal peaks 44 are due to early-cycling off. The classification module 36 then flags this anomaly by assigning a flag value to the anomaly. For example, the classification module 36 assigns a flag value of "1" for an early-cycling off anomaly (this is merely an illustrative example). The classification module 36 sends the flag value to the display component 22, where it is displayed for a medical professional (e.g., a nurse, a doctor, and the like).

In addition, the derivative-based module 34 optionally analyzes the double peak 44 to determine a cycling off time ($t_{soe}$) 50 of the ventilator 10 and a patient effort end time ($T_r$) 52, under the assumption that the first peak corresponds to the ventilator cycling off and the second peak corresponds to the subsequent end of the patient's inspiration effort. For example, as shown in FIG. 2, the first peak 46 has a value of approximately 11.0 cmH$_2$O, and a corresponding $t_{soe}$ 50 of approximately 92 seconds. The second peak 48 has a value of approximately 12.0 cmH$_2$O, and a corresponding $t_r$ of approximately 93 seconds. Alternatively, $t_{soe}$ may be acquired directly by the ventilator 10 as part of the breath cycle information 32 and this may be used to link one peak with the ventilator cycling off. Based on this information, a warning 53 of the detected early cycling off condition is displayed on the ventilator display 22. A medical professional is notified by the warning 53, and the setting of the ventilator 10 can be adjusted by the medical professional so that ventilator 10 cycles off at the same time that patient effort ends (i.e., by making $t_{soe}$ 50 equal to $t_r$ 52). Automatic adjustment by the ventilator 10 is also contemplated, e.g. in the foregoing example the ventilator may increase $t_{soe}$ by 1 second to align with the second peak at 93 sec indicating end of patient inspiration effort. As a result, the first and second peaks 46 and 48 would be equal as well, thereby producing a normal peak 42.

Although the signal 38 has been described in terms of identifying a cycling off anomaly, it will be appreciated that similar features could be used to detect other anomalies, such as active exhalation or double effort. In one embodiment, in the case of active exhalation, the anomaly detection algorithm 28 is programmed to analyze airway pressure measured by the airway pressure sensor 24 to detect a spontaneous respiration anomaly comprising active exhalation as a deviation of an expiratory flow from exponential decay (which is determined from solving the Equation of the Lungs). For example, by solving the Equation of the Lungs during exhalation, the following exponential function is obtained.

$$\dot{V}(t) = \dot{V}(t_{min})\exp(-(t-t_{min})/\tau) \qquad (2)$$

where $t_{min}$ is the time at which the flow reaches its minimum value (negative peak flow $\dot{V}(t_{min})$). $\dot{V}(t_{min})$ and $t_{min}$ are known from the measured flow waveform, $\tau$ is the parameter to be adjusted to fit equation 2. The measured flow waveform during exponential fitting is expected to be a decaying exponential. The natural logarithm is then expected to be a line, as shown in Equation 3 below.

$$\ln(\dot{V}(t)) = a + bt \qquad (3)$$

where a and b are two parameters related to $\dot{V}(t_{min})$, $t_{min}$, and $\tau$ to optimize the fit.

The derivative of the natural logarithm of the flow is then expected to be constant. Changes of such derivative during exhalation are then interpreted as a respiratory anomaly (for instance, patient's active exhalation). The derivative-based module 34 sends this data to the classification module 36. In this example, the classification module 36 is programmed to assign a flag value of "2" for active exhalation occurrences. This flag value is sent to, and displayed on, the display component 22.

In another embodiment, in the case of double effort the anomaly detection algorithm 28 is programmed to analyze airway pressure measured by the airway pressure sensor 24 to detect a spontaneous respiration anomaly comprising a double effort event as a double peak in the airway pressure as a function of time in which at least one peak of the double peak is not coincident with the mechanical ventilator 10 cycling off. Double effort, like early cycling off, is expected to be observed as a double peak in the airway pressure waveform signal during inhalation. In the case of double effort, the second peak is expected to precede the main (largest) peak at the cycle-off point, since it is most likely that the patient will exert both first and second efforts during the inspiration phase. However, the second effort of the double effort may occur elsewhere in the breathing cycle so that the second peak is more randomly located in the single breath. To detect the double effort on the basis of this analysis, the derivative-based module 34 is programmed to calculate instances when the second peak 48 is located away from the main ($t_{soe}$) peak in the signal 38. The derivative-based module 34 is also programmed to calculate the corresponding times of the two peaks of the double effort. The derivative-based module 34 sends this data to the classification module 36. In this example, the classification module 36 is programmed to assign a flag value of "3" for double effort occurrences. This flag value is sent to, and displayed on, the display component 22. In some embodiments, the classification module 36 is programmed to assign a flag value of "0" when no anomaly is detected. This value can be continuously displayed on the display component 22.

Referring back to FIG. 1, the respiratory estimation algorithm 30 is programmed to calculate one or more variables of the Equation of the Lungs (reproduced here):

$$P_{aw}(t) = R\,\dot{V}(t) + EV(t) + P_{mus}(t) + P_0 \qquad (1)$$

As discussed above, the airway pressure sensor 24 is configured to measure $P_{aw}(t)$, and the air flow sensor 26 is configured to measure $\dot{V}(t)$, while V(t) is the inspired air volume calculated as a time integral of air flow $\dot{V}(t)$, and $P_0$ is a constant. The respiratory estimation algorithm 30 is programmed to calculate at least one of R, E, and $P_{mus}(t)$ based on the airway pressure and the air flow as functions of time. The respiratory estimation algorithm 30 is programmed to calculate the values of R, E, and/or $P_{mus}(t)$ and compare them to corresponding threshold values (which are user-configurable on the ventilator 10). Some suitable approaches for optimizing the parameters R, E, and $P_{mus}(t)$ for input V(t) and $P_{aw}(t)$ data are given in: (1) Vicario et al., "Noninvasive Estimation of Respiratory Mechanics in Spontaneously Breathing Ventilated Patients: A Constrained Optimization Approach", *IEEE Trans Biomed Eng.*, 2015 (DOI 10.1109/TBME.2015.2470641); and (2) Al-Rawas et al., "Expiratory Time Constant for Determinations of Plateau Pressure, Respiratory System Compliance, and Total Resistance", *Critical Care*, 17:R23, 2013.

Figure 3:
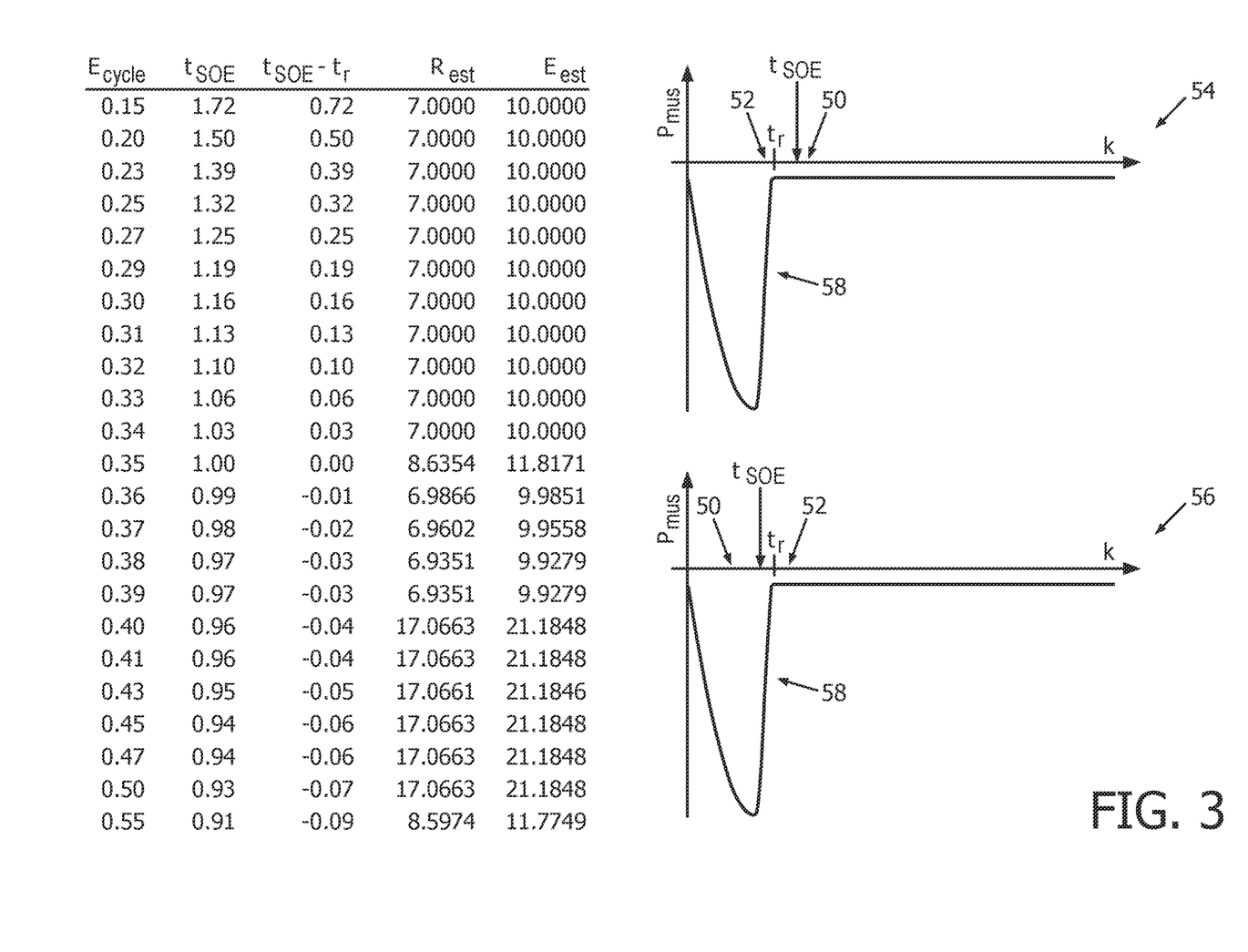
FIG. 3 shows another signal that is analyzed by one or more algorithms of the medical ventilation system of FIG. 1.

The variables R, E, and $P_{mus}(t)$ are optimized by the estimation algorithm 30 to balance the Equation of the Lungs. However, the inventors have found in numerical simulations that such estimation provides values with large error when the ventilator cycles off before the patient's effort is over. For example, FIG. 3 shows an example of respiratory estimation by the algorithm 30 optimizing the parameters R, E, and $P_{mus}(t)$ for simulated V(t) and $P_{aw}(t)$ data, in which the simulation employed R=7.0000, E=10.0000, and a $P_{mus}(t)$ waveform 58 shown on the right-hand side of FIG. 3. FIG. 3 shows the results of simulations where the timing between the ventilator 10 cycling off and $P_{mus}(t)$ is varied by changing the $E_{cycle}$ setting of the ventilator as follows. The ventilator cycles off when the flow, after reaching the maximum positive value $\dot{V}_{max}$ decreases below a threshold given by $E_{cycle}$ times $V_{max}$, with $0<E_{cycle}<1$. Therefore, lower values of $E_{cycle}$ translate into longer time intervals before the ventilator cycles off. For low $E_{cycle}$ values, the ventilator cycles off after the patient's respiratory effort is completed, and the respiratory estimation algorithm 30 is able to estimate R and E exactly as indicated by $R_{est}$=R=7.0000 and $E_{est}$=E=10.0000. This corresponds to the example 54 shown in the upper right of FIG. 3, where $t_{SOE}$ (the time the ventilator cycles off) occurs later than $t_r$ (the end of patient's inspiration effort).

On the other hand, for larger values of $E_{cycle}$ the ventilator shuts off earlier, leading to early cycling off for sufficiently large $E_{cycle}$. Example 56 in the lower right of FIG. 3 shows this early cycling off condition, for which the patient effort end time ($t_r$) 52 occurs after the cycling off time ($t_{SOE}$) 50 of the ventilator 10. In this case, the respiratory estimation algorithm 30 calculates an abnormal values of R and E which begin to vary from their setting values of 7 and 10, respectively. This trend is seen for $E_{cycle}$=0.35 for which $t_{SOE}$=$t_r$ and for higher values of $E_{cycle}$ for which $t_{SOE}$<$t_r$. As disclosed herein, this early cycling off condition can be detected, without estimating $P_{mus}(t)$, by observing a double peak in the airway pressure waveform at $t_{SOE}$. Thus, this condition in which the estimation values $R_{est}$, $E_{est}$ are likely to have large error is detected. (This condition cannot be detected for a real patient by analyzing the output of the estimation algorithm 30 because for a real patient the ground-truth values of R and E are not known a priori).

In some embodiments, the display component 22 is configured to indicate unreliability of the calculated respiratory system variables if an early cycling off anomaly, an active exhalation anomaly, or a double effort anomaly is detected.

For example, the display component 22 is programmed to show the values of R, E, and $P_{mus}(t)$ only when an anomaly is detected. In other embodiments, the display component 22 to continuously display values of R, E, and/or $P_{mus}(t)$ based on the measured airway pressure and airway air flow. As a result, a medical professional can determine when an anomaly is occurring based on the displayed values of, E, and/or $P_{mus}(t)$, in addition to the displayed flag value.

In some embodiments, when an anomaly is detected, the flag value and/or the displayed values of R, E, and $P_{mus}(t)$ conveys to a medical professional that the anomaly is occurring. The medical professional can then adjust the settings of the ventilator 10 so that the anomaly no longer occurs.

In other embodiments, referring back to FIG. 1, a power of breathing (or work of breathing) closed-loop controller 60 is included. The closed-loop controller 60 is programmed to calculate the actual patient's power (or work) of breathing by time integration of the estimated $P_{mus}(t)$ and to adjust the ventilator setting based on the difference between the actual and desired power or work of breathing in order to optimally support the patient's spontaneous respiratory effort. Such a closed-loop controller is described in U.S. Patent Publication No. 2015/0059754, which is incorporated in its entirety herein. In embodiments disclosed herein, the flag output by the anomaly detection algorithm 28 is also input to the closed loop ventilator controller 60. If the flag indicates a respiratory anomaly that makes the output of the respiratory estimation algorithm 30 unreliable (as described with reference to FIG. 3), then the closed loop ventilator controller 60 can take appropriate action, such as maintaining the current ventilator setting in an open-loop fashion, or adjusting ventilator settings based on the detected anomalous condition (e.g. reducing the $E_{cycle}$ setting to bring $t_{SOE}$ into alignment with $t_r$ in the case of early cycling off).

Figure 4:
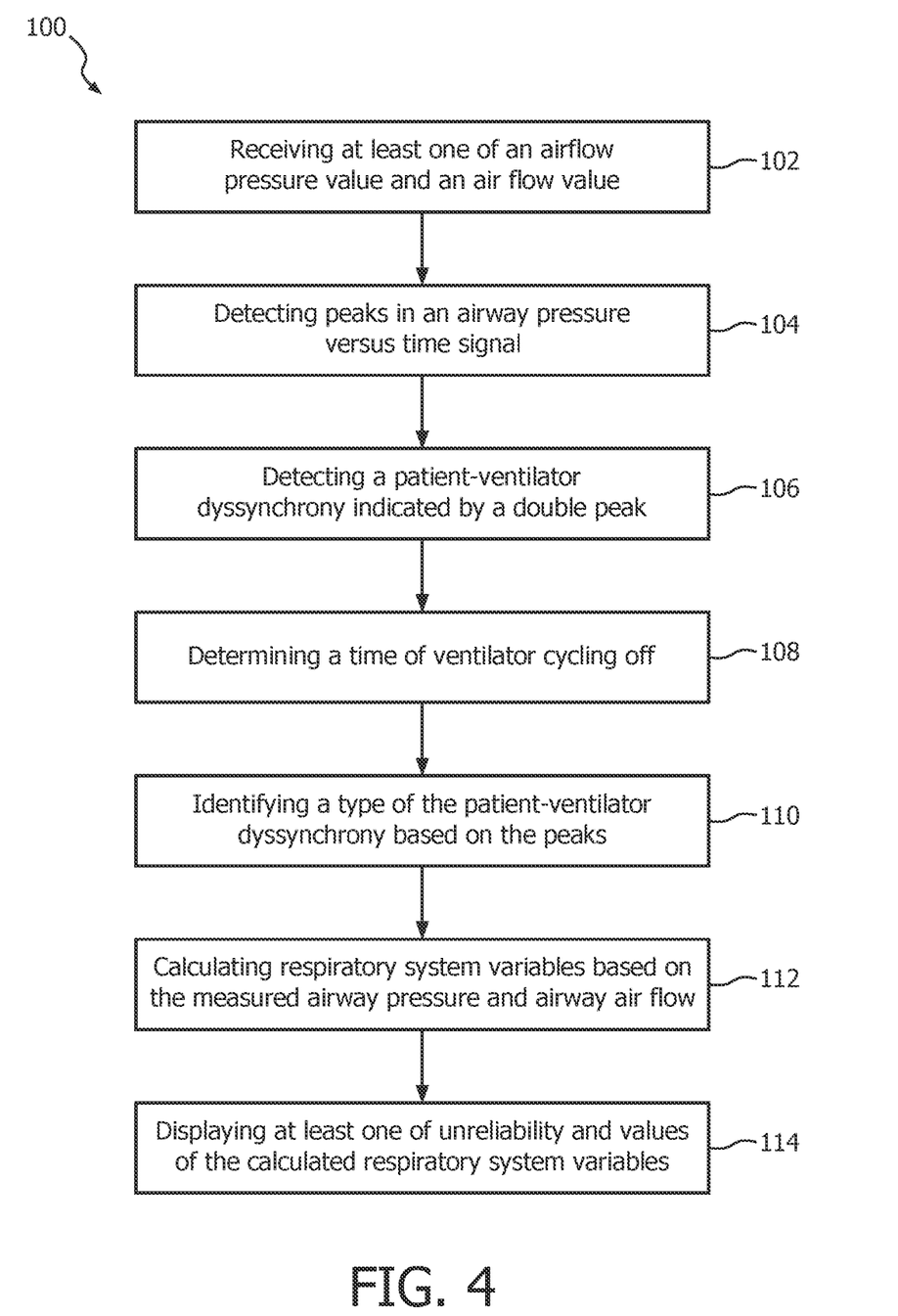
FIG. 4 diagrammatically shows an operations flow chart for the medical ventilation system of FIG. 1.

FIG. 4 shows a method 100 of detecting a spontaneous respiration anomaly. The method 100 includes: receiving at least one of an airflow pressure value and an air flow value from a corresponding airflow pressure sensor 24 and an air flow sensor 26 (step 102); detecting peaks 40, 42, 44 in an airway pressure versus time signal 38 acquired for a patient 12 on a mechanical ventilator 10 (step 104); detecting a patient-ventilator dyssynchrony indicated by a double peak 44 in the airway pressure versus time signal within a single breath (step 106); determining a time 50 of ventilator cycling off from the signal 38 received from a mechanical ventilator 10 or estimated as the time of the largest peak in the ventilator cycle (step 108); identifying a type of the patient-ventilator dyssynchrony based on at least one of: (1) a position of the double peak respective to the time of ventilator cycling off, (2) a position of the second peak of the double peak is after the time of ventilator cycling off, and (3) the double peak being the largest peak in the breath (step 110); optionally calculating one or more respiratory system variables including resistance (R) and/or elastance (E) based on the measured airway pressure and airway air flow in which the detection of the patient-ventilator dyssynchrony does not use the calculated respiratory muscle pressure as a function of time (step 112); and displaying at least one of unreliability of the calculated respiratory system variables if an early cycling off anomaly, an active exhalation anomaly, or a double effort anomaly is detected and values of one or more respiratory system variables including at least respiratory muscle pressure as a function of time based on the measured airway pressure and airway air flow (step 114).

The various data processing components 28, 30 are suitably implemented as a microprocessor programmed by firmware or software to perform the disclosed operations. In some embodiments, the microprocessor is integral to the mechanical ventilator 10, so that the data processing is directly performed by the ventilator 10. In other embodiments the microprocessor is separate from the mechanical ventilator 10, for example being the microprocessor of a desktop computer. The various data processing components 28, 30 of the ventilator settings optimization system may also be implemented as a non-transitory storage medium storing instructions readable and executable by a microprocessor (e.g. as described above) to implement the disclosed operations. The non-transitory storage medium may, for example, comprise a read-only memory (ROM), programmable read-only memory (PROM), flash memory, or other repository of firmware for the ventilator 10. Additionally or alternatively, the non-transitory storage medium may comprise a computer hard drive (suitable for computer-implemented embodiments), an optical disk (e.g. for installation on such a computer), a network server data storage (e.g. RAID array) from which the ventilator 10 or a computer can download the system software or firmware via the Internet or another electronic data network, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A mechanical ventilation device, comprising:
a mechanical ventilator;
at least one airway sensor configured to measure at least one of airway pressure and airway air flow as a function of time for a patient on the mechanical ventilator;
at least one microprocessor programmed to:
analyze at least one of airway pressure and airway air flow measured by the airway sensor to detect a spontaneous respiration anomaly in respiratory muscle pressure as a function of time generated by a patient on the mechanical ventilator;
determine a time of ventilator cycling off from a signal received from the mechanical ventilator; and
identify a type of a patient-ventilator dyssynchrony based on position of peaks detected in the analyzed at least one airway flow and airway pressure respective to the time of ventilator cycling off; and
a display component configured to display an indication of the spontaneous respiration anomaly detected by the at least one microprocessor,
wherein:
the at least one airway sensor includes an airway pressure sensor configured to measure airway pressure as a function of time; and
the at least one microprocessor is programmed to analyze airway pressure measured by the airway pressure sensor to detect the spontaneous respiration anomaly comprising a double effort event as a double peak in the airway pressure as a function of time in which at least one peak of the double peak is not coincident with the mechanical ventilator cycling off.

2. The device of claim 1 wherein: the at least one microprocessor is programmed to analyze airway pressure measured by the airway pressure sensor to detect the spontaneous respiration anomaly comprising an early cycling off event as a double peak in the airway pressure as a function of time coincident with the mechanical ventilator cycling off.

3. The device of claim 2 wherein the at least one microprocessor receives a signal indicative of the mechanical ventilator cycling off and uses the signal to determine a time of the mechanical ventilator cycling off.

4. The device of claim 1 wherein: the at least one microprocessor is programmed to analyze airway pressure measured by the airway pressure sensor to detect the spontaneous respiration anomaly as a double peak in the airway pressure as a function of time within a single breath cycle.

5. The patient monitoring device of claim 1, wherein the at least one airway sensor includes the airway pressure sensor configured to measure airway pressure and the air flow sensor configured to measure airway air flow, and the at least one microprocessor is further programmed to:
calculate one or more respiratory system variables including at least respiratory muscle pressure as a function of time based on the measured airway pressure and airway air flow; and
wherein the detection of the spontaneous respiration anomaly does not use the calculated respiratory muscle pressure as a function of time.

6. The patient monitoring device of claim 5, wherein:
the at least one microprocessor is programmed to detect spontaneous respiration anomalies including at least an early cycling off anomaly, an active exhalation anomaly, and a double effort anomaly; and
the display component is configured to indicate unreliability of the calculated respiratory system variables if an early cycling off anomaly, an active exhalation anomaly, or a double effort anomaly is detected.

7. The patient monitoring device of claim 5, wherein the display component is configured to display values of one or more respiratory system variables including at least respiratory muscle pressure as a function of time based on the measured airway pressure and airway air flow.

8. The patient monitoring device of claim 1, further including a power of breathing closed-loop controller programmed to:
adjust an output of the mechanical ventilator responsive to at least one flag value responsive to a detection of at least one spontaneous respiration anomaly including an early cycling off anomaly, an active exhalation anomaly, and a double effort anomaly.

9. A mechanical ventilation device comprising:
a mechanical ventilator;
at least one airway sensor configured to measure at least one of airway pressure and airway air flow as a function of time for a patient on the mechanical ventilator, wherein the at least one airway sensor includes an airway pressure sensor configured to measure airway pressure as a function of time; and
at least one microprocessor programmed to:
analyze airway pressure measured by the airway pressure sensor to detect a spontaneous respiration anomaly in respiratory muscle pressure as a function of time generated by a patient on the mechanical ventilator, the spontaneous respiration anomaly comprising active exhalation detected as downward slope of the airway pressure following the mechanical ventilator cycling off which is larger than a threshold value;
determine a time of ventilator cycling off from a signal received from the mechanical ventilator; and identify a type of a patient-ventilator dyssynchrony based on position of peaks detected in the analyzed at least one airway flow and airway pressure respective to the time of ventilator cycling off; and a display component configured to display an indication of the spontaneous respiration anomaly detected by the at least one microprocessor.

10. The device of claim 9, wherein: the at least one microprocessor is programmed to analyze airway pressure measured by the airway pressure sensor to detect the spontaneous respiration anomaly as a double peak in the airway pressure as a function of time within a single breath cycle.

11. The patient monitoring device of claim 9, wherein the at least one airway sensor includes the airway pressure sensor configured to measure airway pressure and the air flow sensor configured to measure airway air flow, and the at least one microprocessor is further programmed to:

calculate one or more respiratory system variables including at least respiratory muscle pressure as a function of time based on the measured airway pressure and airway air flow; and wherein the detection of the spontaneous respiration anomaly does not use the calculated respiratory muscle pressure as a function of time.

12. The patient monitoring device of claim 11, wherein:

the at least one microprocessor is programmed to detect spontaneous respiration anomalies including at least an early cycling off anomaly, an active exhalation anomaly, and a double effort anomaly; and the display component is configured to indicate unreliability of the calculated respiratory system variables if an early cycling off anomaly, an active exhalation anomaly, or a double effort anomaly is detected.

13. The patient monitoring device of claim 11, wherein the display component is configured to display values of one or more respiratory system variables including at least respiratory muscle pressure as a function of time based on the measured airway pressure and airway air flow.

14. The patient monitoring device of claim 9, further including a power of breathing closed-loop controller programmed to:

adjust an output of the mechanical ventilator responsive to at least one flag value responsive to a detection of at least one spontaneous respiration anomaly including an early cycling off anomaly, an active exhalation anomaly, and a double effort anomaly.

15. A non-transitory storage medium storing instructions readable and executable by one or more microprocessors to perform a method of detecting a spontaneous respiration anomaly, the method comprising:

detecting peaks in an airway pressure versus time signal acquired for a patient on a mechanical ventilator; and detecting a patient-ventilator dyssynchrony indicated by a double peak in the airway pressure versus time signal within a single breath;

determining a time of ventilator cycling off from a signal received from a mechanical ventilator; and identifying a type of the patient-ventilator dyssynchrony based on position of the double peak respective to the time of ventilator cycling off.

16. The non-transitory storage medium of claim 15, wherein the identifying further includes:

identifying an early cycling off patient-ventilator dyssynchrony based on the position of the second peak of the double peak being after the time of ventilator cycling off.

17. The non-transitory storage medium of claim 15, wherein the method further comprises:

identifying an early cycling off patient-ventilator dyssynchrony based on the double peak being the largest peak in the breath.

18. The non-transitory storage medium of claim 15, wherein the method further comprises: calculating one or more respiratory system variables including at least respiratory muscle pressure as a function of time based on a measured airway pressure and airway air flow; and wherein the detection of the patient-ventilator dyssynchrony does not use the calculated respiratory muscle pressure as a function of time.

19. The non-transitory storage medium of claim 15, wherein the method further comprises:

adjusting an output of the mechanical ventilator responsive to at least one flag value responsive to a detection of at least one spontaneous respiration anomaly including an early cycling off anomaly, an active exhalation anomaly, and a double effort anomaly.

* * * * *